United States Patent [19]

Witt

[11] Patent Number: 4,543,250

[45] Date of Patent: Sep. 24, 1985

[54] TOILETRY FORMULATIONS COMPRISING LOW MOLECULAR WEIGHT CARRAGEENAN

[75] Inventor: Henry J. Witt, Rockport, Me.

[73] Assignee: FMC Corporation, Philadelphia, Pa.

[21] Appl. No.: 483,970

[22] Filed: Apr. 11, 1983

[51] Int. Cl.$^4$ ............... A61K 7/06; A61K 31/70; A61K 35/78

[52] U.S. Cl. ................................ 424/70; 424/74; 514/54; 514/777; 514/783

[58] Field of Search ............ 424/74, 70, 180, 361, 424/364, 195; 426/565, 267, 575; 536/114

[56] References Cited

U.S. PATENT DOCUMENTS

| | | | |
|---|---|---|---|
| 3,378,541 | 4/1968 | Colquhoun et al. | 260/209 |
| 3,849,395 | 11/1974 | Moirano | 536/114 X |
| 4,263,284 | 4/1981 | Schreuder | 424/180 |
| 4,443,486 | 4/1984 | Guiseley | 536/114 X |

FOREIGN PATENT DOCUMENTS

| | | | |
|---|---|---|---|
| 56-150007 | 11/1981 | Japan | 424/361 |
| 57-183709 | 11/1982 | Japan . | |
| 58-4710 | 1/1983 | Japan . | |

OTHER PUBLICATIONS

Chem. Abs. 98:59752y and 98:132146k, (1983).
Merck Index, 9th Ed., #1861, p. 238.
Kirk–Othmer Encyclopedia of Chemical Technology, vol. 17, (Interscience, New York, 2nd Ed., 1968), pp. 774–781.

*Primary Examiner*—Esther M. Kepplinger
*Assistant Examiner*—Shawn P. Foley
*Attorney, Agent, or Firm*—Eugene G. Horsky; Eugene G. Seems

[57] ABSTRACT

Toiletry formulations including low molecular carrageenan extractives which are present in amounts effective to provide for substantivity to hair and skin keratin and provide for conditioning of hair and skin as a result of the water-binding capacity of such extractives.

19 Claims, No Drawings

TOILETRY FORMULATIONS COMPRISING LOW MOLECULAR WEIGHT CARRAGEENAN

The present invention relates to cosmetic and toilet formulations containing naturally occurring sulfated polysaccharide extracts of unusually low water viscosities that are functional in that they impart desirable characteristics to exposed portions of the body; that is the body skin and hair.

Defined broadly, these sulfated polysaccharides are reported as purified from certain red algae (Rhodophyceae class; order Gigartineceae) commonly referred to as carrageenan but also including furcellaran. They have an ester content of about 15% or more and are alternately $\alpha 1-3$; $\beta 1-4$ glycosidically linked. The present invention concerns the use of carrageenans contained within or purified or separated from an appropriate seaweed source. Thus, in the description reference is made to "extractive", "extract," and "extracted," either alone, with, or applied to carrageenan and it will be understood that such terms refer to the carrageenan component of a seaweed, whether such component is in its purified form; that is, physically separated or removed from such seaweed and essentially completely soluble in water, or isolated within treated seaweed particulates which consist primarily of fibrous portions of seaweed that are comprised essentially of cellulose and hemicellulose.

The cosmetic and toilet formulations are especially adapted for use on the external portions of the human body; that is, the body skin and hair, and may be in the form of liquids, lotions, creams or pastes that are applied to such body portions, for example, to clean, soften, lubricate, protect, bulk, and/or impart gloss to surfaces thereof. As hair protrudes from the skin and may well be considered to be part of the skin, and for the sake of simplicity and ease of description, the term "skin" as employed hereinafter is intended to include the hair, scalp, and all exposed body skin portions, even those areas normally lacking hair, such as the palms of the hands.

The teachings of the present invention are applicable to a variety of cosmetic and toilet preparations, hereafter referred to as "toiletry formulations", such as, shampoos, shampoo after-treatment mediums, generally referred to in the trade as "conditioners", hair grooming aids, and cleansing, emollient, hand (healing) liquids, lotions, creams, pastes, and bath products for the skin. In connection particularly with shampoo formulation, reference is made to "surfactant" which is intended to mean any material which has an effect on the surface portions of the skin.

The functionality imparted to the skin by the carrageenan extractive used in the formulations of this invention involves both substantivity; that is, attraction or binding of the hydrated carrageenan to the skin protein, hereafter referred to as "keratin," and conditioning which, as employed herein, refers to physical modification of the skin, such as, its texture, bulk, hold, smoothness, and sheen, which is due to the water-binding and retention capacity of the low water viscosity of the hydrophilic carrageenan extractives employed. Thus, the low viscosity carrageenan extractives of the formulations of the present invention provide for substantivity which, in turn, enables the carrageenan extractives that are bound to the keratin of the skin to exercise their inherent water-binding function.

As a result of the substantivity and conditioning effects achieved by the use of shampoo and/or shampoo after-treatment formulations of the present invention, after drying the cleansed hair exhibits a desirable, softness, body and texture which renders it manageable rather than having an appearance which is often described as "fly-away". When formulations of the present invention are applied to skin areas other than scalp hair, the substantivity and conditioning effects help to impart a soft and smooth texture and appearance. The results achieved are attributed to the hydrophilic character of the carrageenan extractives; that is, their moisture-binding ability, so that skin areas exposed to formulations of the present invention are less subject to overdrying and are capable of retaining moisture. Moreover, the moisture-binding capacity of the carrageenan extractives is of particular importance in shampoo formulations of the present invention as surface moisture on the hair strands serves to dissipate static electricity and thus improve hair manageability. This effect, the dissipation of static electricity, is the direct opposite to that which is often experienced when using polymeric cationic hair conditioners. Of course, lacking the substantivity provided by the low viscosity carrageenan extractives in the formulations of the present invention, conditioning of the skin is negligible, if any, particularly with shampoo and shampoo after-treatment products that contact the hair and scalp for only a short period before being rinsed away.

Of significance is that the low viscosity carrageenan extractives used in the formulations of the present invention are more reactive; that is, bind to hair keratin less rapidly than with the keratin of other skin portions. However, the large surface area of hair exposed to the formulations of this invention permits the desired conditioning effect to be achieved notwithstanding the slower substantivity reaction and short duration of exposure. Actually, the fact that hair is conditioned by these formulations makes clear that formulations of the present invention also provide for conditioning of other skin portions in view of its more active substantivity response. Thus, while the formulations of the present invention are applicable for use on all skin portions, for simplicity and ease of description, the invention is hereafter described with particular emphasis on the substantivity and conditioning effects achieved by shampoo formulations.

In general, conventional shampoos are intended to cleanse hair of surface grease, dirt, and skin debris, yet leave the hair soft, lustrous, and manageable. Surface acting materials (surfactants) provide the necessary cleansing action and, in this respect, soap (salts of fatty acids) give excellent performance but only in the presence of "soft" water. Soaps commonly used in shampoos are precipitated by calcium and magnesium ions which are present in "hard" water, resulting in loss of foaming and cleansing action and forming a dull coating on the hair and scalp.

This problem is avoided in shampoos, and elsewhere, by the use of synthetic detergents and particularly of anionic type, for example, the straight-chain alkyl sulfates, such as, sodium lauryl sulfate and/or triethanolamine lauryl sulfate. These exhibit high foaming or lathering power, even when used in the presence of "hard" water, a characteristic which shampoo users demand.

Anionic detergents are generally preferred over nonionic detergents, such as ethoxylated monyl phenols because of their superior cleansing properties. However, the cleansing action of such synthetic detergents when employed in conventional shampoos is so efficient that they strip away natural oils from the hair and leave it limp, dull, and unmanageable. In order to compensate for this loss of manageability it is desirable to include hair conditioning or finishing ingredients in such preparations to restore manageability to the hair.

Until the present invention, almost without exception, the most effective conditioning materials have been cationic in nature, such as, quaternized derivatives of cellulose or guar gum. Many of such cationic agents are incompatible with the preferred anionic detergents in shampoo formulations. As a consequence, it has been standard practice to offer a separate conditioning formula to be applied to the hair after the shampoo has been rinsed away.

The fact that carrageenan is anionic in nature makes it compatible with the anionic detergents in shampoos and thus makes it possible, but not necessary, to combine both the cleansing and conditioning properties into a single formulation.

The present invention is predicated upon the discovery that carrageenan extractives of very low molecular weight; that is, molecular weights of less than about 100,000, exhibit substantivity and serve admirably as conditioners for skin. These discoveries are indeed surprising considering that carrageenan extractives, albeit of high molecular weight, have been used for many years as shampoo thickeners without any indication of conditioning effects. If it were therefore thought possible to achieve substantivity (and conditioning) between hair, and other skin keratin, and carrageenan extractives it would have long been used in combination with anionic detergents in shampoos, and other skin preparations, for that purpose.

Of still further significance is that the low molecular weight purified carrageenan extractives when utilized in clear anionic shampoo formulations of the present invention maintain a high degree of clarity, even when it is not the case with the substitution of high molecular weight carrageenan extractives in the same formulas. Shampoo clarity is another characteristic generally believed to be preferred by shampoo users.

That substantivity exists between hair and skin protein (keratin) and the low molecular weight carrageenan extractives has not been directly established, nor is such direct evidence necessary to appreciate the merits of the present invention. Based upon the known characteristics of human hair and skin and the characteristics of the low molecular weight carrageenan extractives that are utilized in the formulations of the present invention, the results achieved with such formulations are at least persuasive that substantivity does indeed occur, particu-larly when the pH of the formulations are set below 7.0, and preferably as low as possible compatible with good formulating and dermatological practices, around pH of 4.5 or less. In this respect, the lower the pH of the formulations, the more cationic the keratin becomes and the more reactive is such keratin with the anionic carrageenan extractive contained in such formulations.

More specifically, it is well known that human hair and the outer layer of other skin areas are composed almost entirely of keratin, the protein to which the skin largely owes its physical and chemical characteristics, and that keratin fibers are composed of long polypeptide chains that are cross-linked alternately by peptides, disulfide salt and hydrogen bonds. The degree and combinations of cross-linking generally determines the characteristics and conditions of the skin. As water-wet hair and skin are more easily elongated than when dry, it is assumed that hydrogen bonds between the polypeptide chains are at least weakened. Further, it is generally accepted that such hydrogen bonds, as well as salt linkages, breakdown as a result of disulfide bond ruptures, which may occur, for example, during conventional cosmetic hair treatments, such as permanent waving, bleaching, and oxidative dyeing, as well as by air pollutants, high intensity light, or air oxidation catalyzed by ultra-violet radiation from the sun.

Like all proteins, keratin is amphoteric; that is, it has both positive and negative reactive sites within its chemical structure. It is also common knowledge that the net charge of proteins are a function of the pH of the system in which they reside. Above a certain pH, called the isoelectric point, which is different for and characteristic of each protein type, its net charge is negative and below its isoelectric point a protein's net charge is positive.

As a result, the various bonds between the polypeptide chains which are broken or opened, are believed to be sites at which ionic materials, such as the anionic carrageenan extractives, may readily react or become attached to the hair (and other skin) keratin. Thus, with the rationale expressed, it is possible that the anionic carrageenan extractives, in effect, chemically bond to the hair and/or skin, rather than merely being deposited onto the hair and skin surfaces. Upon binding to the hair keratin, the carrageenan extractives impart body or hold to hair. As heretofore mentioned, this conditioning effect is believed to be due to the water-binding capacity of the carrageenan extractives which results in increased moisture retention by the skin so exposed to the carrageenan extractives.

The presence of a low molecular weight carrageenan extractive in shampoo formulations involves no significant sacrifice in the viscosity, clarity, foaming or cleansing functions of the shampoo formulations, the acid mantle of the scalp, or the softness and sheen of the cleansed and dried hair, yet imparts manageability to the hair.

On the other hand, increased comb drag on water-wet hair has been observed after shampooing with formulations of the present invention when compared to shampoos which differ from such formulations only by the absence of the low molecular weight carrageenan extractives heretofore described. This fact is further evidence that substantivity does indeed occur between the hair keratin and the low molecular weight carrageenan extractives.

As heretofore mentioned, the use of carrageenan extractives in shampoo and other skin formulations is not new as carrageenan extractives of molecular weights well in excess of 100,000, and generally in the molecular weight range of 250,000 to 500,000, have long, but not commonly, been used in a variety of cosmetic and toiletry preparations, including shampoos and lotions, to impart viscosity and slip, features common to many hydrocolloids. If substantivity occurs between such high molecular weight carrageenan extractives and hair and skin keratin it has escaped detection. This is not surprising for in arriving at the present invention it was discovered that the degree of substantivity, or better still the rate of reaction between carrageenan extractives and skin keratin, increases as the molecular weight of the carrageenan extractive is reduced. Considering the short time duration that a shampoo remains in contact with the hair during cleansing, keratin substantivity, if any, of high molecular weight carrageenan extractives is certainly negligible and of no apparent benefit, as evidenced by its lack of recognition.

As heretofore mentioned, the lower the molecular weight of the carrageenan extractive employed in the shampoo formulation, the faster its rate of reaction with the hair keratin. In view of the short time span that a lathered shampoo remains in-situ on the hair during cleansing, it is believed that carrageenan extractives most practical for use in the present invention are those having molecular weights of less than 100,000, and more desirable in the range of from 15,000 to 10,000 and less.

Sulfated seaweed polysaccharides from any source, including all carrageenan fractions, such as kappa, kappa II, lambda, iota, mu, nu, and theta, as well as the closely related Furcellaria and Hypnea types, are suitable for use in this invention once their molecular weights have been reduced to levels as mentioned above.

Various procedures have been described in the art for depolymerizing of hydrocolloids, including carrageenan extractives and related hydrocolloids. The reduction in the molecular weight of these hydrocolloids is readily achieved, as by hydrolysis using acids, such as, acetic or hydrochloric, or by oxidizing agents, such as hydrogen peroxide and ammonium persulfate.

It is known that the water viscosity of a carrageenan extractive increases with its molecular weight, that a relationship exists between the molecular weight and the normal water viscosity of such extractive, and also between the water viscosity and its performance in shampoo and skin formulations of the present invention. Viscosity measurements, hereinafter referred to as water viscosity, are determined by the procedure set forth in Food Chemicals Codex, Third Edition, 1978, published by National Academy Press, and involve an aqueous solution at 75° C. containing a 1.5% by weight concentration of the carrageenan extractive. Most suitable for use in this invention are carrageenan extractives having a water viscosity of not greater than about 5 mPa.s, and preferably less as the lower the water viscosity of the carrageenan extractive the more rapid is the substantivity reaction between such extractive and the hair and skin keratin. Such rapid reaction is, of course, essential in view of the normally short period of time involved in shampooing of hair.

While the low molecular weight carrageenan extractives described are ideally suited for use with liquid shampoos containing an anionic synthetic cleansing agent and in which a high degree of clarity is desired, they are of course well adapted for use with soap-based or amphoteric surfactant-based shampoos and after-shampoo treatment products, and are functional regardless of whether the shampoo is of liquid, liquid creme, or creme lotion form.

In its simplest form a conventional liquid shampoo formulation may contain one or more surfactants as cleansing agents and water. Oils, humectants, and other hair conditioning or finishing ingredients may be included, as well as thickeners, clarifying agents, perfumes, foam stabilizers, and preservatives.

In accordance with the present invention, conventional shampoo and other skin formulations are modified simply by the incorporation of an effective amount of the low molecular weight carrageenan extractive described, either as an addition to or as a partial or total replacement, for example, for the conventional conditioners or finishing agents employed in shampoos or the lubricants or emollients incorporated into skin lotions, creams, and liquids. As carrageenan extractives have demonstrated a synergism with humectants, such as glycerine, and thus improve moisture attraction and retention by the hair and other skin portions, it is desirable, but not esential, that such humectants be included in the formulations of the present invention. In view of this synergism, the efficiency of these non-substantive humectants in attracting moisture to the hair and other skin portions and retaining the same is significantly improved.

By the term "effective amount", and similar terminology as employed herein with reference to low molecular weight carrageenan extractive, is meant the inclusion in formulations of the present invention a sufficient amount of such extractive as will give hair after shampooing and drying a conditioning or manageability effect which is not noticeable in the absence of such extractive; and in the case of formulations applied to skin, gives the skin a soft, supple, and smooth appearance. As heretofore mentioned, most suitable for use in this invention are carrageenan extractives having a water viscosity of about 5 mPa.s or less, and that the lower the molecular weight, and thus the water viscosity, of the carrageenan extractive employed, the more rapid is its reaction with the hair protein.

Accordingly, the effective amount of carrageenan extractive incorporated into skin formulations will vary directly with its water viscosity and the degree of hair and/or skin conditioning desired, For example, satisfactory hair conditioning has been achieved as a result of shampooing hair for a period of about 15–30 seconds with a formulation containing water and, by weight, about 15% of a conventional synthetic anionic surface cleansing agent and about 0.25% to about 1.5% of a carrageenan extractive having a water viscosity of about 5 mPa.s. Amounts of 0.25% to about 1.5%, by weight, of a carrageenan extractive having a water viscosity of about 5 mPa.s or less may also be incorporated into formulations applied to the skin. As skin keratin is less cross-linked than hair keratin, it follows that it is more reactive; and since skin formulations remain in contact with the skin for relatively longer periods, lesser amounts of carrageenan extract may be incorporated in such skin formulations with satisfactory results being achieved. If the carrageenan extractives in such shampoo and skin formulations are replaced by carrageenan extractives having lower water viscosities, the amount of such replacement extractives used may be reduced without apparent sacrifice in the hair or skin conditioning effect that is achieved. Alternatively, if the amount of carrageenan extractive is kept constant, greater conditioning effect may be achieved and, in the case of shampoo formulation, the period of shampooing may be reduced.

Incorporating more than about 2%, by weight, of the slowest reacting low molecular weight carrageenan extractive (water viscosity of about 5 mPa.s) in a shampoo or other skin formulation provides for no significant improvement in the conditioning of the cleansed hair or skin and for economic reasons, alone, should be avoided.

To better illustrate the merits of the present invention, reference is made to the following Examples which illustrate formulations containing carrageenan characterized as having a water viscosity in a 1.5%, by weight, aqueous solution at 75° C. of 1.5 mPa.s. The formulations of the present invention set forth below and corresponding formulations having no low molecular weight carrageenan, hereinafter referred to as "conventional formulation(s)", were put to test on the hair and skin of persons who were not made aware as to which of the respective formulations were those of the present invention.

EXAMPLE I

The shampoo formulation I had a viscosity of 8000 mPa.s, a pH of 4.5, and surfactant actives level of 11.9%. The test subjects reported that, as compared with the conventional formulation, water-wet hair shampooed with shampoo formulation I exhibited greater comb drag, which is indicative of substantivity, and, after drying, the hair was reported to have a higher sheen, softer texture, and was much more manageable.

EXAMPLE II

After comparative testing of shampoo formulation II and the conventional formulation, the test subjects reported that, in addition to the results attained with shampoo formulation I, the manageability of the hair improved, this being evidence of conditioning.

EXAMPLE III

The after-shampoo hair conditioner formulation III had a pH of 3.5 and was a pourable, opaque emulsion that was applied to and retained on the hair for a brief period after shampooing with a conventional shampoo formulation, and then rinsed out. Hair treated with this formulation III exhibited a high sheen, soft texture, and was highly controllable; that is, no flyaway.

EXAMPLE IV

Use of the hand and body lotion formulation IV by test subjects resulted in excellent skin softening and moisturizing effects, which was believed to exceed those obtained upon use of a conventional formulation.

FORMULATIONS

I. Shampoo

| | |
|---|---|
| 30.00 | Ammonium lauryl sulfate (28%) (anionic surfactant) |
| 10.00 | Cocamidopropyl betaine (35%) (amphoteric surfactant) |
| 0.15 | Glycolic acid (70%) (part of buffer system) |
| 0.35 | Disodium phosphate (part of buffer system) |
| 0.10 | DMDM hydantoin (preservative) |
| 1.00 | Carrageenan (hair control) |
| qs | Water, color, fragrance |
| 100.00% | |

II. Shampoo with Humectant
Shampoo formulation of I above, together with 1.0% glycerin.

III. After-Shampoo Hair Conditioner

| | |
|---|---|
| 1.50 | "Promulgen D" - Americhol Corp - (Stearyl Alcohol and Ceteareth-20 - nonionic surfactant) |
| 2.00 | "Arlacel 165" - ICI Americas Inc. - Glyceryl Stearate and PEG-100 Stearate - nonionic surfactant) |
| 1.00 | Cetearyl Alcohol (viscosity control) |
| 1.50 | "Emulan HF" - BASF AG - (heavy fraction mink oil, for sheen and wet-combability) |
| 1.00 | Glycerin (humectant) |
| 0.50 | "Polyox WSRN 80" - Union Carbide Co. - (PEG-5M) (for wet-combability) |
| 1.50 | Carrageenan (hair control) |
| 0.04 | Disodium phosphate (part of buffer system) |
| 0.25 | 70% glycolic acid (part of buffer system) |
| 0.15 | DMDM hydantoin (preservative) |
| qs | Water, Color, fragrance |
| 100.00% | |

IV. Hand and Body Lotion

| | |
|---|---|
| Phase A | |
| 4.0 | Glyceryl stearate SE (emulsifier/emulsion stabilizer) |
| 1.0 | Myristyl myristate (viscosity control) |
| 2.0 | Stearic acid XXX (part of O/W soap emulsifier) |
| 0.5 | Lanolin alcohols (W/O auxiliary emulsifier) |
| 6.0 | Mink oil (emollient) |
| 0.2 | Preservative |
| Phase B | |
| 0.5 | Triethanolamine (part of O/W soap emulsifier) |
| 5.0 | Polyethylene glycol-400 (humectant) |
| 1.0 | Carrageenan (skin conditioner) |
| 79.8 | Water |
| 100.00% | |

Add 80° C. Phase A to 70° C. Phase B. Cool with high sheer agitation to 40° C. Develops rich cream-lotion viscosity after 24 hours.

I Claim:

1. A toiletry formulation for application to body skin which comprises a sulfated seaweed polysaccharide extractive of low molecular weight in combination with a conventional toiletry preparation selected from the group consisting of shampoos, shampoo after-treatment mediums, hair grooming aids, cleansing agents, emollient agents, healing agents and bath products, said extractive being characterized in that the water viscosity thereof in a 1.5%, by weight, water solution at 75° C. is not greater than about 5 mPa.s., said extractive being present in an amount effective to have substantivity with the skin keratin and to provide for conditioning of such skin by its moisture-binding capacity.

2. A toiletry formulation as defined in claim 1 wherein said extractive comprises not less than about 0.25% by weight, of said formulation.

3. A toiletry formulation as defined in claim 1 wherein the viscosity of the 1.5%, by weight, water solution of said extractive at 75° C. is less than 5 mPa.s.

4. A toiletry formulation as defined in claim 1 wherein said extractive is a carrageenan.

5. A toiletry formulation as defined in claim 1 wherein said extractive comprises from about 0.25 to 1.5%, by weight, of said formulation.

6. A toiletry formulation as defined in claim 4 wherein said carrageenan extractive comprises not less than about 0.25%, by weight, of said toiletry formulation.

7. A toiletry formulation as defined in claim 4 further including glycerine as a humectant.

8. A toiletry formulation as defined in claim 4 wherein said toiletry formulation has a pH of less than 7.

9. A toiletry formulation as defined in claim 4 wherein the viscosity of the 1.5%, by weight, solution of said carrageenan extractive at 75° C. is less than 5 mPa.s.

10. A toiletry formulation as defined in claim 4 wherein said low molecular weight carrageenan extractive is substantially soluble in water.

11. A toiletry formulation as defined in claim 10 wherein the viscosity of the 1.5%, by weight, water solution of said carrageenan extractive at 75° C. is less than 5 mPa.s.

12. A toiletry formulation as defined in claim 9 wherein said carrageenan extractive comprises not less than about 0.25%, by weight, of said toiletry formulation.

13. A toiletry formulation as defined in claim 6 wherein said carrageenan extractive comprises from about 0.25 to 1.5%, by weight, of said toiletry formulation.

14. A toiletry formulation as defined in claim 13 further including glycerine as a humectant.

15. A toiletry formulation as defined in claim 8 wherein said toiletry formulation has a pH of not greater than about 4.5.

16. A toiletry formulation as defined in claim 15 wherein said carrageenan exractive comprises not less than about 0.25%, by weight, of said toiletry formulation.

17. A toiletry formulation as defined in claim 16 wherein said carrageenan exractive is substantially soluble in water.

18. A toiletry formulation as defined in claim 15 wherein said carrageenan extractive comprises not less than 0.25%, by weight, of said toiletry formulation and has a viscosity in a 1.5%, by weight, water solution of less than 5 mPa.s.

19. A toiletry formulation as defined in claim 13 wherein said toiletry formulation has a pH not greater than about 4.5.

* * * * *